United States Patent
Paaske et al.

(10) Patent No.: US 8,708,941 B2
(45) Date of Patent: Apr. 29, 2014

(54) ADJUSTABLE MULTI-COMPONENT HIP ORTHOSIS

(75) Inventors: Gregory J. Paaske, Eustis, FL (US); Shannon R. Schwenn, Deltona, FL (US); Benjamin G. Domb, Hinsdale, IL (US)

(73) Assignee: Orthomerica Products, Inc., Orlando, FL (US)

( * ) Notice: Subject to any disclaimer, the term of this patent is extended or adjusted under 35 U.S.C. 154(b) by 167 days.

(21) Appl. No.: 13/346,599

(22) Filed: Jan. 9, 2012

(65) Prior Publication Data

US 2013/0178775 A1 Jul. 11, 2013

(51) Int. Cl.
*A61F 5/00* (2006.01)

(52) U.S. Cl.
USPC .............................. 602/23; 602/16

(58) Field of Classification Search
USPC ........ 602/5, 16, 19, 23–24, 26–27; 601/5, 23, 601/34; 128/876, 99.1, 100.1, 101.1; 2/311–312, 321
See application file for complete search history.

(56) References Cited

U.S. PATENT DOCUMENTS

| | | | |
|---|---|---|---|
| 5,421,810 A | 6/1995 | Davis et al. | |
| 5,460,599 A | 10/1995 | Davis et al. | |
| 5,814,001 A | 9/1998 | Schwenn et al. | |
| 6,589,195 B1 | 7/2003 | Schwenn et al. | |
| 7,048,707 B2 | 5/2006 | Schwenn et al. | |
| 7,473,235 B2* | 1/2009 | Schwenn et al. | 602/16 |
| 7,597,672 B2 | 10/2009 | Kruijsen et al. | |
| 2010/0262056 A1* | 10/2010 | Lusky et al. | 602/19 |
| 2012/0289878 A1* | 11/2012 | Schwenn et al. | 602/23 |

FOREIGN PATENT DOCUMENTS

| | | |
|---|---|---|
| EP | 1588678 | 10/2005 |
| WO | 2011/066323 | 6/2011 |

OTHER PUBLICATIONS

European Application No. 13150073.8 Extended European Search Report dated May 13, 2013, 5 pages.

* cited by examiner

*Primary Examiner* — Tatyana Zalukaeva
*Assistant Examiner* — Ophelia A Hawthorne (57) ABSTRACT

A hip orthosis having a flexible waist band for conforming to the waist of a user can be attached at any position on the exterior of the waist band with adjustments in a vertical circumferential and rotational position for connecting a hip support unit at a desired position to maintain the head of a femur into the acetabulum of a user. The hip support unit is connected to a hinge member and an extension unit that is secured at a lower portion of the thigh wherein a thigh support unit can be adjusted so that a three point force system can be applied to the user.

16 Claims, 7 Drawing Sheets

ADJUSTABLE MULTI-COMPONENT HIP ORTHOSIS

BACKGROUND OF THE INVENTION

1. Field of the Invention

The present invention is directed to an adjustable multi-component orthosis to provide an adjustable body support portion for conforming to a patient's body configuration such as a low profile hip orthosis for post-surgery treatment of a patient who has had a hip arthroscopy procedure.

2. Description of Related Art

An orthosis which can conform to a particular body configuration has required a customized orthosis made from body measurements of a patient. However, medical and insurance costs have significantly increased and the provisions of pre-manufactured orthosis that can be adjusted by an orthotist shave become more popular.

An example is an orthotic to provide support for the body after replacement of a hip joint or hip arthroplasty, which is a surgical procedure in which a hip joint is replaced by a prosthetic implant. A femoral component can be replaced with a metallic or ceramic artificial femoral head where ceramic bearing surfaces are frequently employed to address any wear issue and relieve possible problems from osteolysis that can occur from acrylic bone cement and wear debris.

Risks that are involved in the surgery are a potential for blood clots in the legs, infections, and nerve damage. Generally it is desirable to have the patient start moving and walking as soon as possible to prevent complications. Postoperative hip orthoses have been known to reduce the incidences of dislocation in both patients who have undergone a primary hip replacement and also patients that have required a subsequent hip revision. Reference can be made to a clinical report, Orthotic Management of Hip Dislocation using a Newport™ hip orthosis by Dulcey Lima.

Orthopedic hip configurations have been utilized for various purposes such as a leg abductor to resist muscular contractions as shown in U.S. Pat. No. 5,814,001. U.S. Pat. No. 6,589,195, U.S. Pat. No. 7,048,707 are examples of hip orthoses for permitting an orthotic management when the hip joint has been compromised with the capability of controlling flexion and extension internal and external rotation adduction and abduction. In such an environment, the hip joint is a synovial ball and socket joint that generally consists of an articulation of the spherical head of the femur with a cup like shape of the acetabulum. The acetabular labrum attaches to a bony rim of the acetabulum and cups around the head of the femur to hold it firmly in place. Various ligaments add strength to the articulation of the hip joint and a large number of muscles act on the hip joint. The gluteus medius is primarily associated with abduction. The anterior fibers assist with flexion and internal rotation. Posterior fibers assist with the extension and external rotation. These respective muscle groups stabilize the pelvis during a single leg support.

However, these muscle groups can be compromised when surgical procedures are performed at the hip joint such as a hip replacement surgery. A significant problem that occurs when a hip joint has been compromised is the possibility of subsequent dislocation of the hip joint. Thus, the femoral head can be driven out of the acetabulum. For example, the hip can be most susceptible to posterior dislocation when it is flexed past 90°, internally rotated and adducted. These movements can occur in everyday life, such as by sitting on a low chair and leaning forward while putting weight on an affected hip joint and internally rotating when coming to a standing position. Thus, common activities of daily living, specifically excessive hip flexion with loaded extremity and internal rotation on the affected side can cause dislocation. Anterior dislocation can also occur when a hip is externally rotated, abducted and flexed. For example, if there is an external force such as the knee being hit or subject to an accidental contact with an object, the neck of the femur or the greater trochanter levers the femur out of the acetabulum. Thus, an orthosis must be able to effectively control the limits of extension rotation in a patient who has experienced an anterior dislocation.

Additionally, as the population becomes older, there are more occasions for the treatment of hip disorders and there is still a need to improve the function of such orthoses and their component parts in the medical field in an economical manner while addressing a comfort level for the patient to encourage maximum prolonged usage.

Efforts have also been made to encourage early mobility of a patient after a hip surgery and it is desirable to enable the patient to easily don a hip orthosis with appropriate compression with a lightweight structure. It is still necessary for the hip orthosis to provide adequate rigidity to stabilize the hip with preferably a configuration that would encourage prolonged use by the patient. U.S. Pat. No. 7,473,235 is an example of a lightweight prophylactic hip orthosis. U.S. Pat. No. 7,597,672 discloses a hip orthosis with a rotable leaf spring for the user to actuate after donning the hip orthosis.

Orthopedic surgeons have now developed new techniques for repairing the hip joint that can often provide pain relief and postpone or eliminate the need for total joint replacement. This procedure, hip arthroscopy, utilizes an extremely small and long camera called an arthroscope that allows the surgeon to visualize the inside of the joint without the need for an open surgical procedure. Traction is applied to the foot to distract the hip joint so that sufficient space can be created between the hip joint surfaces to insert specialized instruments. Arthroscopy uses a variety of "shavers" used to debride the frayed labrum or cartilage, and uses specialized tools to reconnect and repair soft tissue, and incorporates fluoroscopy to determine the precise location of the surgical instruments. Fluid is inserted through the hip joint to both clear debris and improve visualization for the surgeon. Hip arthroscopy is a less invasive procedure with significantly less soft tissue trauma than the traditional open surgical procedures such as total hip replacement (arthroplasty).

Hip arthroscopy can treat labral tears in the labrum cuff of thick tissue that surrounds and supports the hip joint. Additionally, if pieces of cartilage form within the hip joint they can be removed by lavage and rough edges in the hip joint can be scraped and smoothed. Additionally, the synovial lining of the hip joint can be addressed if inflamed.

While a hip arthroscopy procedure can frequently be performed as an outpatient procedure without spending days in a hospital, it is still necessary to rehabilitate the muscles around the joint to make them stronger to assist the weight-bearing surfaces within the hip joint and increase the range of motion of the hip joint. The proper use of exercise in the recovery process encourages healing and failure to exercise and move on the hip joint can even lead to permanent disability.

There is still a need in the medical industry to provide a relatively lightweight and multi-component low profile orthosis that can be easily adjusted to meet the needs of the patient, for example in the post treatment of hip arthroscopy patients that can be readily adjustable by the orthotist for the particular patient while being lightweight and of a low profile to encourage prolonged use by the patient and effectively protect any compromised hip joint.

SUMMARY OF THE INVENTION

The present invention provides a multi-component adjustable hip orthosis that can be customized to a particular user to provide a relatively lightweight orthosis.

A hip engaging unit includes a flexible waist band that includes a post and pulley system to multiply the forces applied in attaching the waist band to the user. A pair of attachable first and second waist band segments can be appropriately cut and reattached to the post and pulley system mounted at the rear of the waist band. Anchor tabs connected to a nylon line extends through a series of pulleys to provide a mechanical force advantage in tightening the waist band on the waist of the user.

A strap fastener is adhered to a semi-rigid hip paddle that can be removably attached to the flexible waist band to adjust both a vertical, circumferential and rotational positioning on a particular user. The hip paddle is connected to an adjustable hinge that can limit adduction and abduction movement of the user's leg. An adjustable extension unit can position a thigh support unit of a flexible cushioned oblong member for applying a force against the femur of the user. The lower end of the adjustable extension unit is attached to a thigh engaging unit whereupon the hip engaging unit can apply a lateral force to the user's pelvis opposite a surgical site while the thigh engaging unit can apply a force on a distal side of a femur. The thigh support unit laterally presses the femur of the user on the surgical side whereby a force is transmitted through the femur and the pelvis to push the head of the femur into the acetabulum of the user when a hip engaging unit and a thigh engaging unit are fastened to the body of the user.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures and components have not been described in detail as not to unnecessarily obscure aspects of the present invention.

Referring to FIGS. 1 through 4, a preferred embodiment of the present invention is disclosed wherein a low profile multi-component orthosis 2 includes a hip engaging unit 4, a removable hip support unit 5, a thigh engaging unit 6, an adjustable extension unit 8 and a thigh support unit 10. The hip engaging unit 4 includes an adjustable waist band unit 12 with a force multiplying connector post and pulley system 14 that can be removably attached respectively to a first waist band segment 16 and a second waist band segment 18. The respective first and second waist band segments, 16, 18, can be cut to conform to the user's waist size.

The hip engaging unit 4 further includes a semi-rigid hip paddle 20 with a strap fastener 22 appended to the semi-rigid hip paddle 20 for attachment as the hip support unit 5, to an exterior surface of one of the first waist band segment 16 and the second waist band segment 18 in an adjustable manner to accommodate the particular dimensions and size of the user. The strap fastener 22 can adhere over a patient's hip joint at any position in a vertical, circumferential and rotational position on the waist band 12 to provide freedom in mounting the semi-rigid hip paddle 20.

Figure 1:
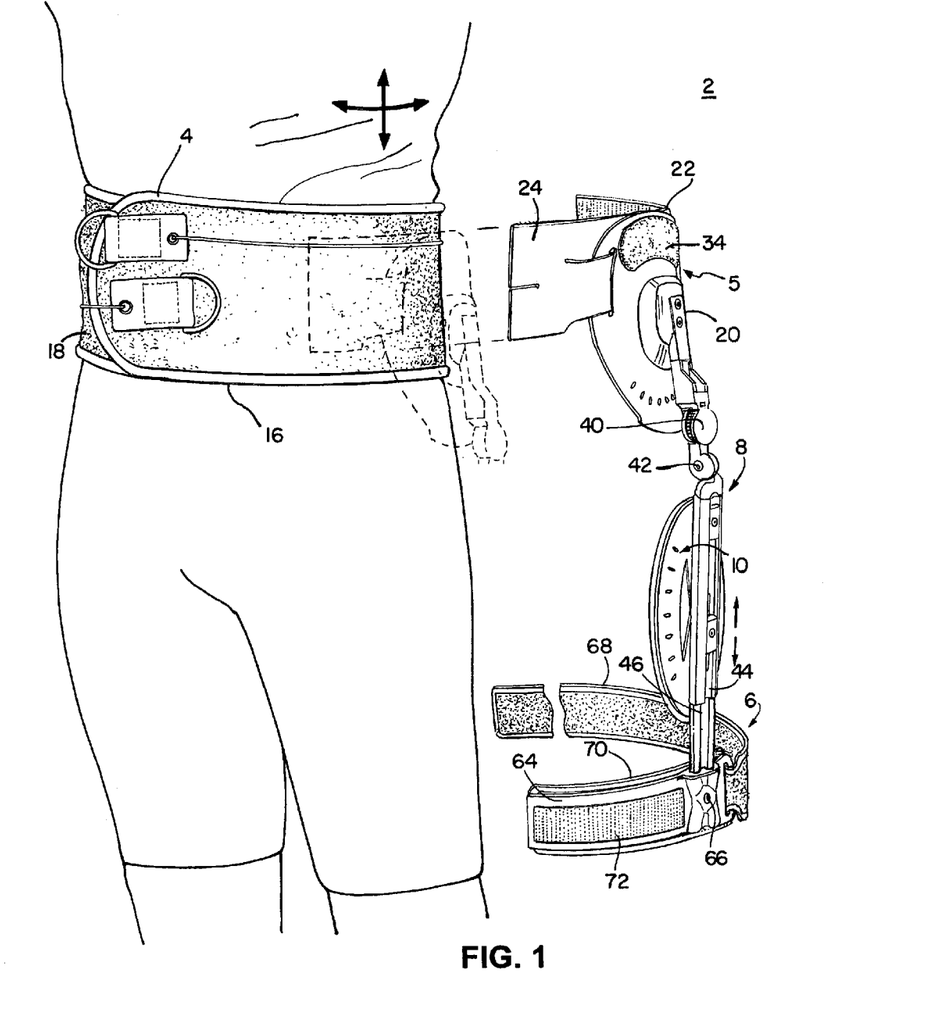
FIG. 1 is a partial perspective view of a multi-component orthosis with phantom lines showing an attachment to the waist band.

As can be seen in FIG. 1, the adjustable waist band 12 is mounted on a user or patient and, as will subsequently be described, can be adjusted to accommodate the user's dimensions by a physician or an orthotist. The orthotist will appropriately align the semi-rigid hip paddle 20 so it can provide a stable support surface to apply a controlled force component to help retain a femoral head of the pelvis into the user's acetabulum.

Figure 2:
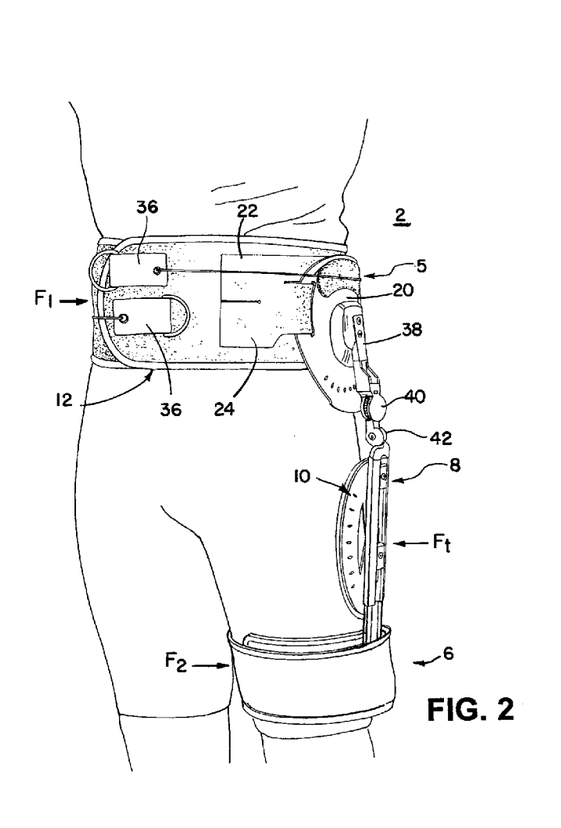
FIG. 2 is a perspective view showing the orthosis mounted on a user.

In FIG. 2, the low profile orthosis 2 of the present invention provides a three point pressure or force system over the proximal thigh for stabilizing the trochanter into the acetabular socket, thereby preventing a dislocation while maintaining a comfortable fit to ensure an extended use by the user. Thus, a prophylactic orthosis 2 is provided to assist the recovery period of the user while maintaining a limited size orthosis, avoiding discomfort to the patient and firmly providing the necessary leg movement limitations and protection during the recovery period. The user is encouraged to engage in early mobility to prevent deterioration of muscles. As a result of this three point pressure system, our low profile orthosis 2 provides pressure forces to the body of the user at three separate points, namely a lateral pelvis position $F_1$, opposite the surgical site, the femur, Ft, on the side of the surgical site, and a distal femur position, $F_2$, also on the opposite side from the surgical site. Overall, these respective forces translate through the femur and pelvis, thereby stabilizing the head of the femur into the pelvic socket (acetabulum) during physical activity.

Figure 6:
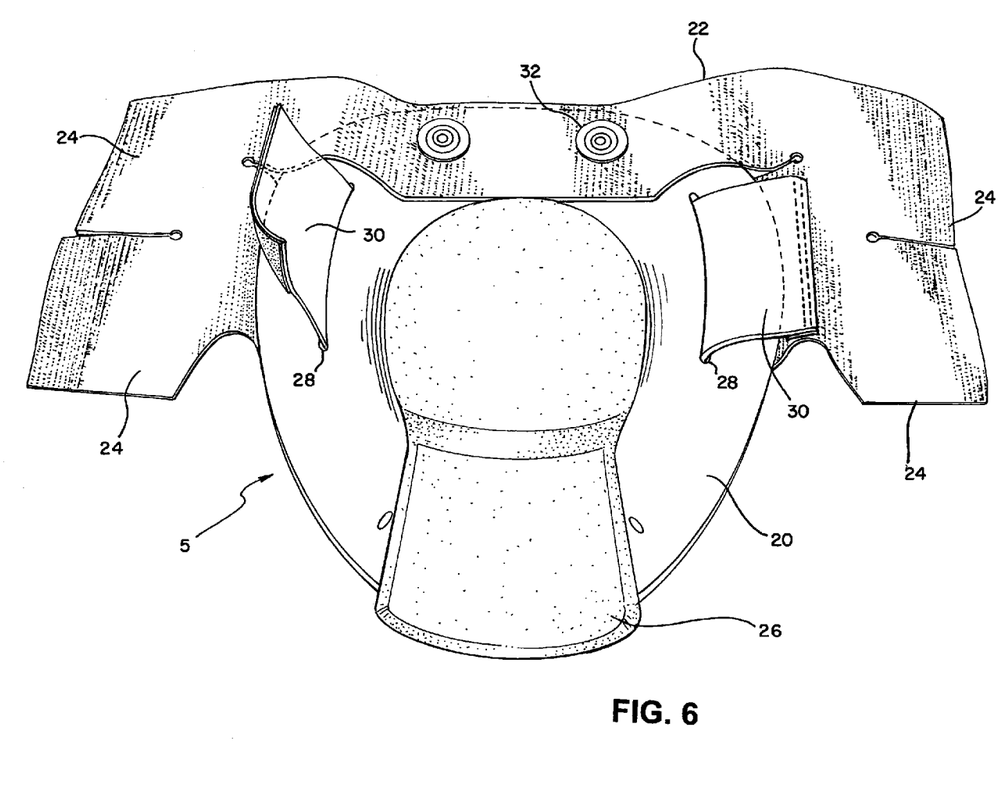
FIG. 6 is a perspective view showing an interior of the semi-rigid hip paddle.
Figure 7:
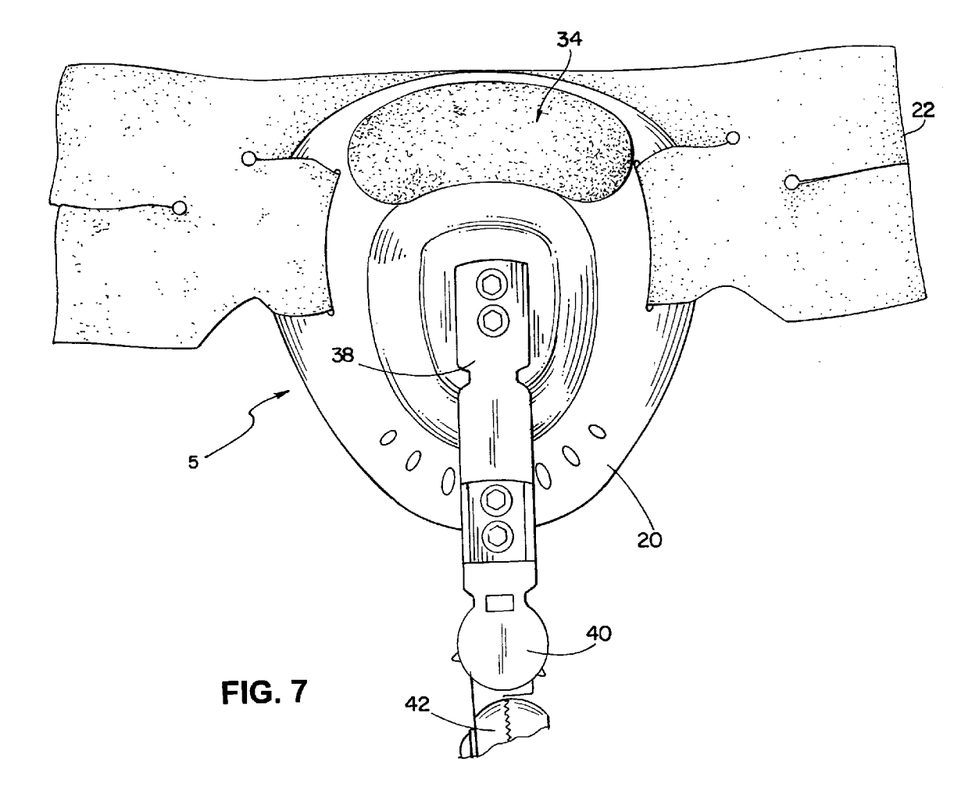
FIG. 7 is a perspective view of the exterior of the semi-rigid hip paddle.

As seen in FIGS. 1, 6 and 7, the combination of the semi-rigid hip paddle 20 and the strap fastener 22 are components of the hip support unit 5 to enable an exterior surface adhesion with an exterior surface of one of the first waist band segment 16 and the second waist band segment 18. Our multi-component orthosis is not only adjustable to the size of the patient, but also can be optionally mounted on either the right or left hip of the patient depending on the specific surgical site.

As can be seen in FIGS. 6 and 7, a flexible fastening strap 22, for example of a hook and nap material, can strongly adhere to an exterior surface of the waist band 12. Hook and nap materials can be purchased under the trademark Velcro®, with the hook material capable of adhering onto the nap material and strongly resisting any shearing force attempting to remove the hook material from the nap material. As can be appreciated, the hook material can be pulled apart in a perpendicular direction from the nap material to permit a release between these components.

As shown in FIG. 2, the hook portions on the interior surface of our strap fastener 22 can strongly adhere the hip paddle 20 to the waist band 16 on the patient and movement of the patient's leg would not generate a sufficient perpendicular release force. The flexible nature of our strap fastener 22 permits adjustment to different waist sizes of the user. The provision of a plurality of flaps 24, for example a pair of flaps 24 on each end of the strap fastener 22, further accommodates an adjustment fastening for potentially different dimensions of users. As can be appreciated, our orthosis is designed to be customized in an efficient manner by an orthotist and thereby avoid the requirement and cost of a customized manufactured orthotic.

Figures 5A, 5B:
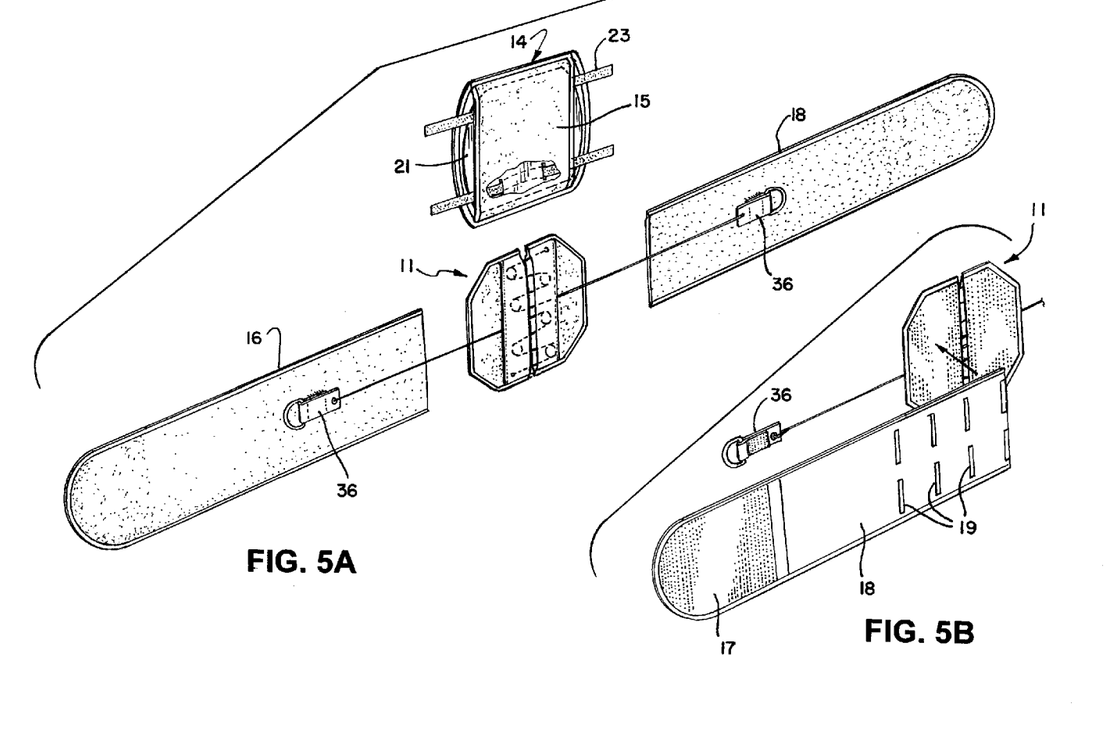
FIGS. 5A and 5B are an exploded explanatory view disclosing the component parts of the adjustable waist band.

FIG. 5 is an exploded view wherein FIG. 5A discloses the respective adjustable waist band 12 including the first waist band segment 16 and the second waist band segment 18. The second waist band segment has nap material on the outside or exterior surface and fastening hook material 17 adjacent one end. The patient can fasten the waist band 12 by attaching the hood material 17 to overlap the exterior nap material on the adjacent waist band segment 16. Sizing indicator marks 19 are provided on the interior side of each of the respective first and second waist band segments 16 and 18 to enable an orthotist to cut the respective waist band segments to a specific size of a patient equally on both waist band segments. Thus, equivalent sizing indicators 19 are also provided on the first and second waist band segment.

A post and pulley system 14 includes a sleeve or cover member 15 that can receive a pair of pulley segments 11. A thin plastic sheet 21 provides a sliding surface that can be anchored within the cover member 15 and a set of four elongated tabs 23 can be attached, two to each side, of the pulley members 11 for mounting them within the cover 15 and permitting relative movement across the surface of the plastic sheet 21. A nylon line is anchored respectively on each half of the pulley segments 11 with posts extending across to provide the configuration of the pulley system. The nylon lines are attached to anchor tabs 36 with hook material so that pulling on the nylon lines will cause the respective halves of the pulley segments 11 to be pulled together. Since the pulley halves are also provided with a hook material which can adhere to the nap material on the respective ends of the first waist band segment 16 and the second waist band segment 18, an appropriate adjustment to provide a multiplication of the forces for tightening the waist band can be accomplished. FIG. 5B discloses the hook side of the pulley segments 11 which can be applied to the respective waist band segments 16, 18.

Figure 3:
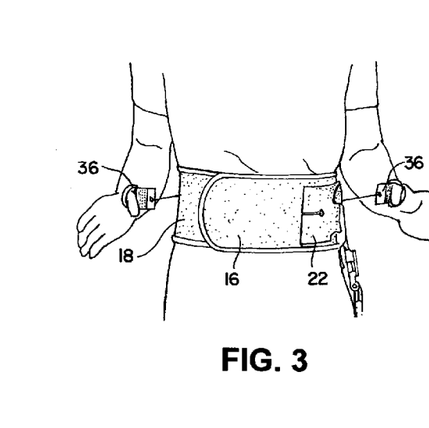
FIG. 3 is a perspective view showing an orthosis waist band being tightened by the user.

Accordingly, a user, as shown in FIG. 3, can insert his/her thumbs through appropriate rings on the anchor tabs 36 for tightening the waist band 12 so that it can establish a firm attachment of the semi-rigid hip paddle 20 at the desired location. As can be seen in FIG. 2, the anchor tabs 36 are attached to the outer exterior surface of the nap material of the adjustable waist band 12.

Figure 4:
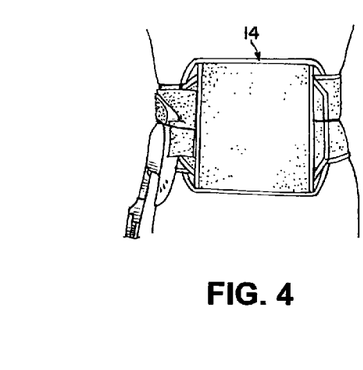
FIG. 4 is a rear view of the orthosis on a user.

FIG. 4 discloses a rear view of the post and pulley system 14 wherein the ends of the respective first waist band segment 16 and second waist band segment 18 can be adjusted with an application of force that is a multiplication of the force actually applied by pulling the nylon lines.

Referring to FIG. 6, an interior elevated view of the semi-rigid hip paddle 20 and the strap fastener 22, forming the adjustable hip support unit 5, are disclosed. The hip paddle 20 is a molded 13% glass filled nylon with a flexural modulus of 350,000 psi to provide structural support and a degree of firmness. Centrally mounted on the hip paddle 20, which has an approximately triangular perimeter, is a cushion pad 26 of a soft rubbery type of material that is adhered to a central portion of the hip paddle 20 by an appropriate adhesive. The cushion pad 26 extends below the lower edge of the hip paddle 20. A pair of curved slots 28 have sufficient openings to permit lower tabs 30, integrally formed as a part of the strap fastener 22 to be fitted to extend through, as shown on the left hand side, and to be adhered by adhesive and/or stitching to provide an anchor portion on each side of the strap fastener 22 to the hip paddle 20. The upper portion of the strap fastener 22 is secured by rivets 32 which provide a further positive anchoring of the strap fastener 22 to the hip paddle 20. The expanded hook surface area of the strap fastener 22 forms a U-shape configuration above the relatively rigid hip paddle 20 to provide adequate adhesion to the nap material on the waist band 12.

Life cycling tests were performed by attaching the orthosis 2 to an analog of a human pelvis and right leg with a mechanical joint which permits the simulated right leg to pivot and be driven by a motor. The leg on the test apparatus is connected to a motor which causes the leg to swing through an arc which starts with the leg pointed as if it is in a "straight down" (parallel to the spine) position and is swung upward (as if lifting a knee in the direction of the chest) by 45 degrees.

The orthosis 2 was placed on the test apparatus and the flexion stop was set to 40 degrees to cause the hook and nap attachment area of stop fastener 22 to the waist band 12 to be repetitively stressed, because the leg is moving through a greater arc than the hinge joint on the orthosis thereby inducing forces and stresses on the attachment area.

In addition, the orthosis hinge joint was placed in 30 degrees of abduction. The test apparatus was oriented on its side (as if the "person"/analog was laying on their side). The 30 degrees of abduction causes the mechanical leg to be suspended upward in the air (as if a person was laying on their left side with their right leg pointed up at an angle in the air), with the weight of the analog leg hanging and cantilevered at a distance from the joint itself, thereby inducing forces and stresses. After 300,000 cycles, there were no signs of a detaching of the nap and hook material between the strap fastener 22 and waist band 12.

The respective pair of flaps 24 are cut into the respective ends of the strap fastener 22 to provide more adjustability in adhering the strap fastener 22 to the appropriate waist band segment 16, 18. The interior side of the strap fastener 22, including each of the flaps 24, preferably have a hook configuration. Referring to the exterior side of the hip paddle 20 and the strap fastener 22, a nap material is utilized. A curved swatch 34 of nap material is adhered to the upper exterior surface of the hip paddle 20. Providing a nap material on the exterior side further facilitates providing an expanded surface area about the user's waist to which the anchoring tabs 36 can be fastened when the waist band 12 is tightened.

As can be seen in FIG. 7, a mounting bracket 38 is anchored by bolts in a central area of the hip paddle 20. A rubbery cushion pad 26, on an interior side, is shown in FIG. 6 and covers a companion fastening element for the mounting bracket 38. The mounting bracket 38 in FIG. 2, extends downward and is connected to a hinge 40, for example of a type disclosed in U.S. Pat. No. 5,460,599. Other hinge designs could be utilized such as U.S. Pat. No. 5,421,810. A releasable ball joint member 42 is connected to the lower half of the hinge 40 to permit a relative adjustment of the adjustable extension unit 8 from the user's side.

Figure 8:
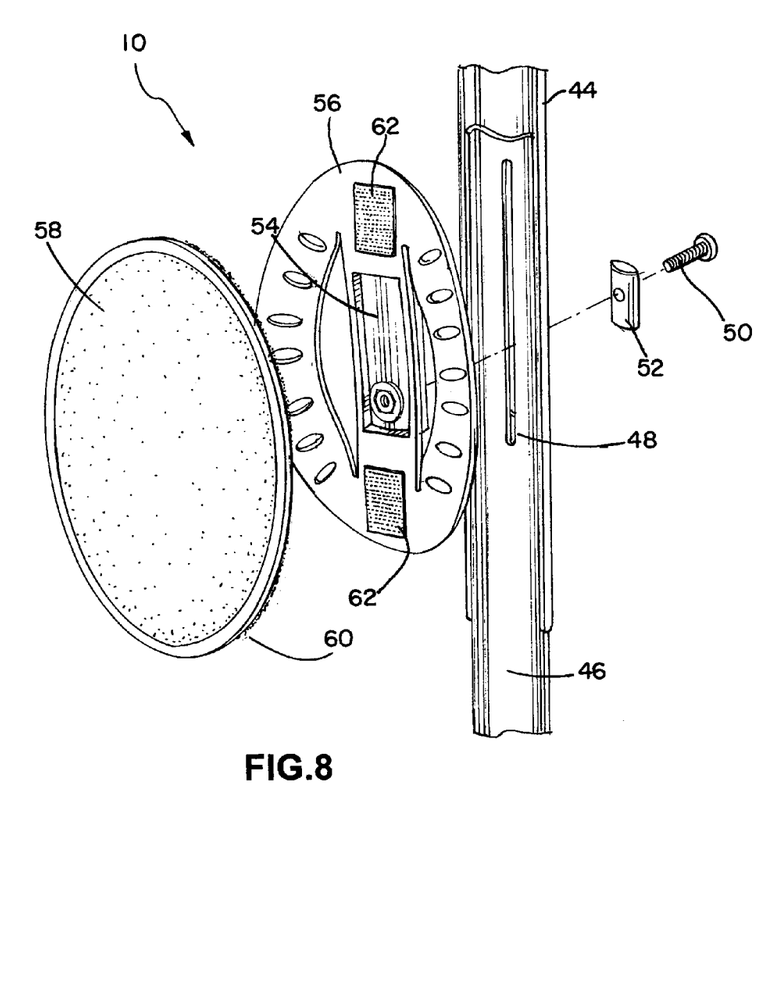
FIG. 8 is an exploded perspective view of an adjustable extension unit and thigh support unit.

Referring to FIG. 8, an exploded view of the adjustable extension unit 8 and thigh support unit 10 is disclosed. A pair of slidable lightweight metal extension members 44 and 46 with a cross sectional W shape are nestled together to adjust the vertical length of the adjustable extension unit 8 and to further provide a position to anchor the thigh support unit 10 at an appropriate location. Elongated slots 48 are provided into each of the extension members 44, 46 with a size to permit an appropriate fastener bolt 50 and slidable spacer member 52 to interconnect with a bracket member 54 that is anchored to a relatively flexible concave paddle member 56 formed from a plastic material such as nylon or polypropylene with a flexural modulus of 152,000 psi. The bracket member 54 and paddle member 56 can be molded together with the bracket member 54 having reinforcing ribs (not shown) and the paddle member 56 has a thinner flexible configuration with parallel slits to provide more side flexibility to form a flexible cushioned oblong member.

The adjustable extension unit 8 is sandwiched between the bracket member 54 and the spacer member 52 and is held in place by the bolt 52 and a threaded aperture in the bracket member 54.

A soft and washable compression fabric pad 58 can both cushion a contact surface with the user's thigh while providing ventilation in a relatively light structure. An interior side of the compression fabric pad 58 has a nap configuration 60 for removably adhering to a pair of hook pads 62 attached to the paddle member 56.

The extension members 44 and 46 can be formed, for example, of aluminum extrusions to create a telescoping assembly with basically a cross-sectional W shape. The interior extension member 44 is slidably mounted with a conforming W shape to be captured by inwardly projecting side rails on the exterior extension member 46. The interior telescoping extension member 44 in turn is anchored to the thigh engaging unit 6 as seen in FIG. 1. Thus, the adjustable extension unit 8 enables a firm fastening between the waist and thigh of the user.

Figure 9:
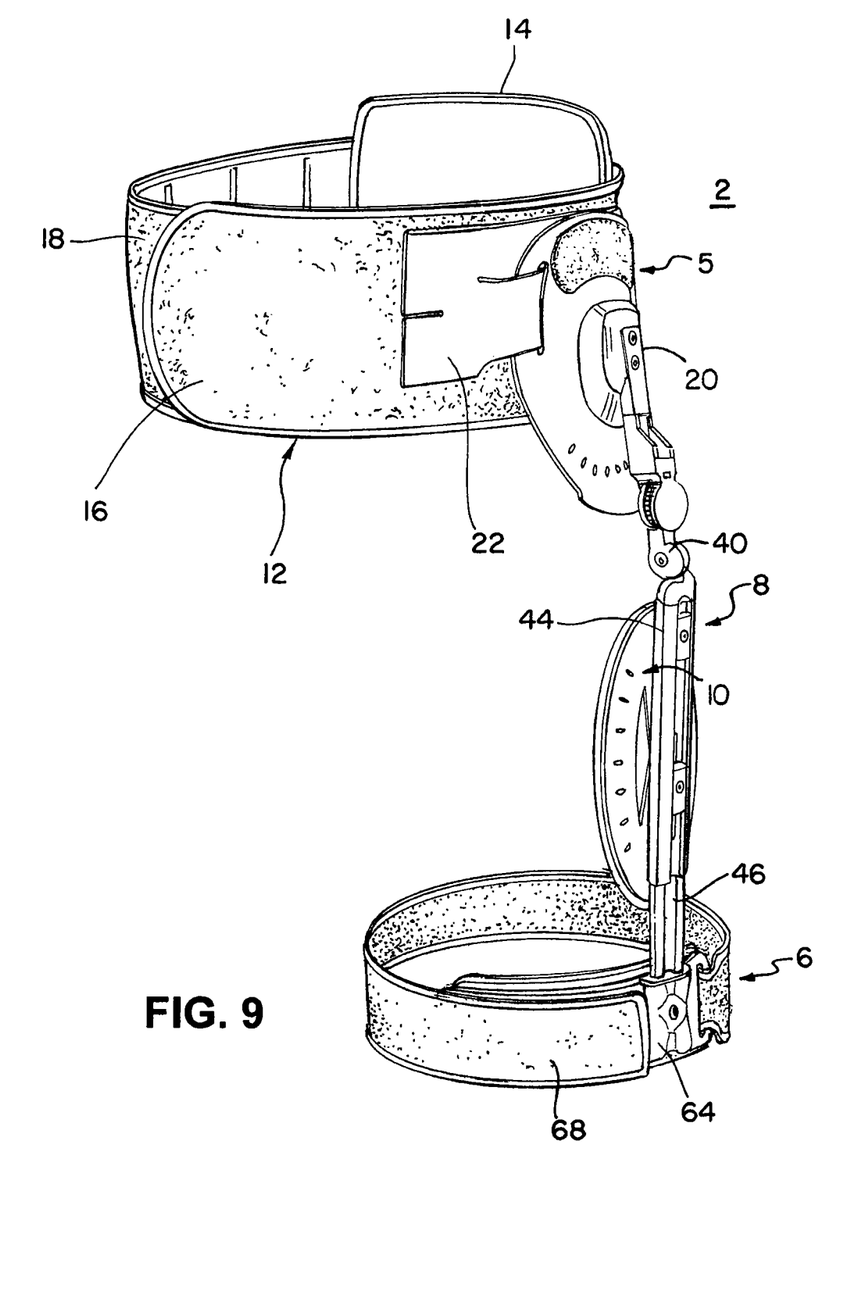
FIG. 9 is a perspective view of a multi-component orthosis in an assembled format.

The thigh engaging unit 6 may comprise a one piece flexible polypropylene (flexural modulus, 152,000 psi) injection molded malleable thigh strap member 64 of a C shape with a vertically open W shaped aperture for capturing an end of the extension member 46, see FIG. 1 and FIG. 9. A screw 66 anchors the thigh strap member 64 to the end of extension member 46 while permitting a limited vertical pivotal movement to facilitate adjusting onto the thigh of the user. An extended flexible strap 68 is fastened to an aperture in the thigh strap member 64 with nap material on the interior and the exterior of the strap 68. The strap 68 is initially provided with enough length that it could be cut to a specific size. The thigh strap member 64 has strips of hook material on both the interior and exterior sides. The interior side can capture a washable compression pad 70 for contacting the user's thigh. The exterior hook material 72 can adhere to the nap material on the strap 68 for closing and encapturing the thigh of the user.

FIG. 9 discloses the multi-component orthosis 2 with the adjustable waist band 12 in a closed configuration and the thigh engaging unit 6 in a closed configuration.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A postoperative hip orthosis comprising:
a hip engaging unit including a flexible waist band for adjustably conforming to a waist of a user about the user's pelvis, the flexible waist band includes first and second waist band segments and a force multiplying connector for varying a displacement distance between respective ends of the first and second waist band segments to provide a multiplication of the forces for tightening the first and second flexible waist band segments about the waist of the user for securing the hip engaging unit on the waist of the user to enable a lateral force to be applied to the user's pelvis opposite a surgical site;
a thigh engaging unit including a malleable thigh member for conforming to a thigh of a user, to engage a femur of the user on the surgical site side and on a distal side of the femur;
an adjustable extension unit connected to the hip engaging unit and the thigh engaging unit to enable adjustment to accommodate a size of the user's leg and waist;
a thigh support unit connected to the adjustable extension unit at a position between the hip engaging unit and the thigh engaging unit to engage and laterally press the femur of the user, on the surgical side, whereby a force is translated through the femur and pelvis to push a head of the femur into the acetabulum of the user when the hip engaging unit and thigh engaging unit are fastened to the user; and
a hip support unit removably connectable at a surface position on the flexible waist band for appropriately anchoring the adjustable extension unit to the hip engaging unit to accommodate a dimension of the user,
wherein the hip support unit includes a semi-rigid concave paddle member configured to extend over a user's hip joint for exerting a force against the hip joint and a flexible strap, permanently connected to the semi-rigid concave paddle member, for an adjustable adhering to one of the first and second waist band segments at any position across the one of the first and second waist band segments in a vertical, circumferential and rotational position to provide freedom in alignment with the head of the user's femur in the acetabulum, the flexible strap extends across an upper surface of the semi-rigid concave paddle member and beyond adjacent sides of the semi-rigid concave paddle member, and
wherein the flexible strap has one of a hook and nap material and the one of the first and second waist band segments has another of the hook and nap material to enable a removable fastening between the flexible strap and an exterior surface of one of the first and second waist band segments, while maintaining an operative fixation to the user during the postoperative recovery period.

2. The postoperative hip orthosis of claim 1 wherein the thigh support unit includes an oval concave paddle with a flexural modulus of less than half the concave paddle member of the hip support unit.

3. The postoperative hip orthosis of claim 2 wherein the oval concave paddle has a pair of slits aligned in parallel with the adjustable exterior unit to provide a flexible contact with the thigh of the user.

4. The postoperative hip orthosis of claim 1 wherein the flexible strap has a plurality of flaps to facilitate adherence to the flexible waist band.

5. The postoperative hip orthosis of claim 1 wherein the flexible strap has a hook material covering a U-shape area and the one of the first and second waist band segments has a nap material to enable a removable fastening between the flexible strap and an exterior surface of one of the first and second waist band segments.

6. The postoperative hip orthosis of claim 1 wherein the malleable thigh member has a C-shape to engage the thigh with a flexural modulus of less than half a flexural modulus of the concave paddle member of the hip support unit.

7. The postoperative hip orthosis of claim 1 wherein the adjustable extension unit includes a pair of elongated members that overlap and are mounted for telescoping movement, wherein the pair of extension elongated members have an approximately W cross-sectional shape with an outer extension member capturing an interior extension member.

8. A postoperative hip orthosis comprising:
a hip engaging unit including a flexible waist band for adjustably conforming to a waist of a user about the user's pelvis, the flexible waist includes first and second waist band segments and a connector for enabling a varying displacement between respective ends of the first and second band segments and a closure unit for securing the hip engaging unit on the waist of the user to enable a lateral force to be applied to the user's pelvis opposite a surgical site;
a thigh engaging unit including a malleable thigh member for conforming to a thigh of a user, to engage a femur of the user on the surgical site side and on a distal side of the femur;
an adjustable extension unit connected to the hip engaging unit and the thigh engaging unit to enable adjustment to accommodate a size of the user's leg and waist;
a thigh support unit connected to the adjustable extension unit at a position between the hip engaging unit and the thigh engaging unit to engage and laterally press the femur of the user, on the surgical side, whereby a force is translated through the femur and pelvis to push a head of the femur into the acetabulum of the user when the hip engaging unit and thigh engaging unit are fastened to the user; and
a hip support unit removably connectable at a surface position on the flexible waist band for appropriately anchoring the adjustable extension unit to the hip engaging unit to accommodate a dimension of the user,
wherein the hip support unit includes a concave paddle member configured to extend over a user's hip joint for exerting a force against the hip joint and a flexible strap, permanently connected to the concave paddle member for adhering to one of the first and second waist band segments at any position across the one of the first and second waist band segments in a vertical, circumferential and rotational position to provide freedom in alignment with the head of the user's femur in the acetabulum, the flexible strap extends across an upper surface of the concave paddle member and beyond adjacent sides of the concave paddle member, and
wherein the flexible strap has one of a hook and nap material and the one of the first and second waist band segments has another of the hook and nap material to enable a removable fastening between the flexible strap and an exterior surface of one of the first and second waist band segments, while maintaining an operative fixation to the user during the postoperative recovery period.

9. The postoperative hip orthosis of claim 8 wherein the flexible strap has a hook material covering a U-shape area and the one of the first and second waist band segments has a nap material to enable a removable fastening between the flexible strap and an exterior surface of one of the first and second waist band segments.

10. The postoperative hip orthosis of claim 9 wherein the flexible strap has a plurality of flaps to facilitate adherence to the flexible waist band.

11. The postoperative hip orthosis of claim 9 wherein the oval concave paddle has a pair of slits aligned in parallel with the adjustable exterior unit to provide a flexible contact with the thigh of the user.

12. The postoperative hip orthosis of claim 8 wherein the malleable thigh member has a C-shape to engage the thigh with a flexural modulus of less than half a flexural modulus of the concave paddle member of the hip support unit.

13. The postoperative hip orthosis of claim 8 wherein the thigh support unit includes an oval concave paddle with a flexural modulus of less than half the concave paddle member of the hip support unit.

14. A hip orthosis comprising:
a flexible hip engaging unit including a flexible waist band for adjustably conforming to a waist of a user about the user's pelvis;
the flexible waist band includes first and second waist band segments and a closure unit for fastening the first and second flexible waist band segments about the waist of the user for securing the flexible hip engaging unit on the waist of the user to enable a lateral force to be applied to the user's pelvis opposite a surgical site;
a thigh engaging unit for conforming to a thigh of a user, to engage a femur of the user on a distal side of the femur;
an adjustable extension unit connected to the hip engaging unit and the thigh engaging unit to enable adjustment to accommodate a size of the user's leg and waist;
a thigh support unit connected to the adjustable extension unit at a position between the hip engaging unit and the thigh engaging unit to engage and laterally press the femur of the user whereby a force is translated through the femur and pelvis to push a head of the femur into the acetabulum of the user when the hip engaging unit and thigh engaging unit are fastened to the user; and
a hip support unit, removably connectable at a surface position of the hip engaging unit for appropriately anchoring the adjustable extension unit to the hip engaging unit to accommodate dimensions of the user,
wherein the hip support unit includes a semi-rigid concave paddle member configured to extend over a user's hip joint for exerting a force against the hip joint and a flexible strap, permanently connected to the semi-rigid concave paddle member, for an adjustable adhering to one of the first and second waist band segments at any position across the one of the first and second waist band segments in a vertical, circumferential and rotational position to provide freedom in alignment with the head of the user's femur in the acetabulum, the flexible strap extends across an upper surface of the semi-rigid concave paddle member and beyond adjacent sides of the semi-rigid concave paddle member, and
wherein the flexible strap has one of a hook and nap material and the one of the first and second waist band segments has another of the hook and nap material to enable a removable fastening between the flexible strap and an exterior surface of one of the first and second waist band segments, while maintaining an operative fixation to the user.

15. The hip orthosis of claim 14 wherein the flexible material is a flexible strap of hook material and the hip engaging unit is a flexible waist band including nap material.

16. The hip orthosis of claim 15 wherein the flexible strap has a plurality of flaps to facilitate adherence to the flexible waist band.

* * * * *